(12) United States Patent
O'Bear et al.

(10) Patent No.: US 9,841,377 B2
(45) Date of Patent: Dec. 12, 2017

(54) SAMPLE TEST CARDS

(75) Inventors: Raymond O'Bear, Granite City, IL (US); Brian Livingston, St. Louis, MO (US); David Hertlein, Sunset Hills, MO (US); Richard Scott Remes, Chesterfiled, MO (US); Stanley M. Philipak, Augusta, MO (US)

(73) Assignee: bioMerieux, Inc., Durham, NC (US)

( * ) Notice: Subject to any disclaimer, the term of this patent is extended or adjusted under 35 U.S.C. 154(b) by 0 days.

(21) Appl. No.: 13/302,455

(22) Filed: Nov. 22, 2011

(65) Prior Publication Data

US 2012/0141325 A1    Jun. 7, 2012

Related U.S. Application Data

(60) Provisional application No. 61/416,557, filed on Nov. 23, 2010.

(51) Int. Cl.
*G01N 21/64* (2006.01)
*B01L 3/00* (2006.01)

(52) U.S. Cl.
CPC ........ *G01N 21/6452* (2013.01); *B01L 3/5025* (2013.01); *B01L 2200/0642* (2013.01); *B01L 2300/0816* (2013.01); *B01L 2300/0864* (2013.01)

(58) Field of Classification Search
CPC .............. G01N 21/6452; B01N 3/5025; B01N 2200/0642
See application file for complete search history.

(56) References Cited

U.S. PATENT DOCUMENTS

| | | |
|---|---|---|
| 3,957,583 A | 5/1976 | Gibson et al. |
| 3,963,355 A | 6/1976 | Aldridge et al. |
| D243,542 S | 3/1977 | Fadler et al. |
| D243,543 S | 3/1977 | Fadler et al. |
| 4,038,151 A | 7/1977 | Fadler et al. |
| 4,116,775 A | 9/1978 | Charles et al. |
| 4,118,280 A | 10/1978 | Charles et al. |
| D254,687 S | 4/1980 | Fadler et al. |

(Continued)

FOREIGN PATENT DOCUMENTS

| | | |
|---|---|---|
| AU | 722698 B2 | 8/2000 |
| WO | WO2009121037 | 10/2009 |

OTHER PUBLICATIONS

Chinese Office Action and Search Report dated Aug. 20, 2014 for patent application No. 201180050246.4.

(Continued)

*Primary Examiner* — Sam P Siefke
(74) *Attorney, Agent, or Firm* — Alston & Bird LLP

(57) ABSTRACT

The present invention is directed to sample test cards having an increased sample well capacity for analyzing biological or other test samples. In one embodiment, the sample test cards of the present invention comprises a fluid channel network disposed in both the first surface and the second surface and connecting the fluid intake port to the sample wells, the fluid channel network comprising at least one distribution channels, a plurality of fill channels operatively connected to the at least one distribution channel, a plurality of through-channels operatively connected to one or more of the fill channels and a plurality of horizontally orientated fill ports operatively connecting the fill channels to the sample wells.

18 Claims, 3 Drawing Sheets

(56) References Cited

U.S. PATENT DOCUMENTS

| | | |
|---|---|---|
| 4,318,994 A | 3/1982 | Meyer et al. |
| 4,806,316 A | 2/1989 | Johnson et al. |
| 5,340,747 A | 8/1994 | Eden |
| 5,374,395 A | 12/1994 | Robinson et al. |
| 5,609,828 A | 3/1997 | O'Bear et al. |
| D382,647 S | 8/1997 | Staples et al. |
| 5,746,980 A | 5/1998 | O'Bear et al. |
| 5,762,873 A | 6/1998 | Fanning et al. |
| 5,766,553 A | 6/1998 | Staples et al. |
| 5,856,193 A | 1/1999 | Fanning et al. |
| 5,869,005 A | 2/1999 | O'Bear et al. |
| 5,888,455 A | 3/1999 | Seaton et al. |
| 5,891,396 A | 4/1999 | Karl et al. |
| 5,932,177 A | 8/1999 | O'Bear et al. |
| D414,272 S | 9/1999 | O'Bear et al. |
| 5,951,952 A | 9/1999 | O'Bear et al. |
| 5,965,090 A | 10/1999 | Fanning et al. |
| 6,024,921 A | 2/2000 | Freiner et al. |
| 6,045,758 A | 4/2000 | Staples et al. |
| 6,086,824 A | 7/2000 | Fanning et al. |
| 6,136,270 A | 10/2000 | Maes et al. |
| 6,156,565 A | 12/2000 | Maes et al. |
| 6,485,690 B1 | 11/2002 | Pfost et al. |
| 7,601,300 B2 | 10/2009 | Blanton et al. |
| D689,780 S | 9/2013 | O'Bear et al. |
| D689,781 S | 9/2013 | O'Bear et al. |
| D689,782 S | 9/2013 | O'Bear et al. |
| D690,216 S | 9/2013 | O'Bear et al. |
| D714,172 S | 9/2014 | O'Bear et al. |
| 2003/0180191 A1 | 9/2003 | Suzuki et al. |
| 2004/0206408 A1* | 10/2004 | Peters et al. .......... 137/825 |
| 2005/0048597 A1 | 3/2005 | Smith et al. |
| 2007/0014695 A1* | 1/2007 | Yue et al. .......... 422/100 |
| 2008/0257754 A1 | 10/2008 | Pugia et al. |
| 2012/0088263 A1 | 4/2012 | Bruno et al. |

OTHER PUBLICATIONS

English language translation of Examiner's comments for the Chinese Office Action for patent application No. CN201180050246.4.

International Search Report and Written Opinion for Application No. PCT/US11/61893 dated Mar. 29, 2012.

International Search Report and Written Opinion for Application No. PCT/US11/55078 dated Apr. 27, 2012.

* cited by examiner

SAMPLE TEST CARDS

CROSS REFERENCE TO RELATED APPLICATION

This application claims the benefit of U.S. Provisional Patent Application No. 61/416,557, entitled, "Improved Sample Test Cards", filed Nov. 23, 2010, which is incorporated herein.

FIELD OF THE INVENTION

The invention relates to improved sample test cards, which have an increased sample well capacity for analyzing biological or other samples.

BACKGROUND OF THE INVENTION

Sample test cards have been used to analyze blood or other biological samples in a spectroscopic or other automated reading machine. Such machines receive a small test card, roughly the size of a playing card, in which biological reagents, nutrients or other material is deposited and sealed, prior to injection of patient samples.

The test card contains the reagents and receives the patient samples in a series of small wells, formed in the card in rows and columns and sealed, typically with tape on both sides. The test cards are filled with patient sample material through fine hydraulic channels formed in the card. The microorganisms in the samples may then be permitted to grow or reactions to proceed, generally over a period of up to a few hours, although the period varies with the type of bacteria or other substance analyzed and sample used.

The current assignee has commercialized instruments for fast, accurate microbial identification, and antimicrobial susceptibility testing (e.g., Vitek® 2 and Vitek® Compact). These instruments include an incubation stations that maintains sample test cards at a precisely controlled temperature to enhance microorganism growth in the individual sample wells. The incubation station includes a rotating carousel that has a plurality of slots for receiving test sample cards. The carousel is vertically mounted and rotates about a horizontal axis. This rotation about the horizontal axis during incubation causes the test card to be rotated through 360° from a normal "upright" card position, through an "inverted" or "upside-down" card position and then back again to an "upright" position. After the incubation, the samples contained in the wells are placed in front of a laser, fluorescent light or other illumination source. The content of the sample in a given well can then be deduced according to readings on the spectrum, intensity or other characteristics of the transmitted or reflected radiation, since the culture of different bacteria or other agents leave distinctive signatures related to turbidity, density, byproducts, coloration, fluorescence and so forth. The instruments for reading the test cards and the incubation carousel are further described in U.S. Pat. Nos. 5,762,873; 5,888,455; 5,965,090; 6,024,921; 6,086,824; 6,136,270; 6,156,565; and 7,601,300, the contents of which are incorporated herein by reference herein.

Despite the general success of test cards in this area, there is an ongoing desire to improve the performance of the cards and readings on their samples. It is for example an advantage to impress more reaction wells in a given card, so that a greater variety of reactions and therefore discrimination of samples can be realized. A given facility may have only one such machine, or be pressed for continuous analysis of samples of many patients, as at a large hospital. Conducting as many identifying reactions on each sample as possible is frequently desirable, yielding greater overall throughput.

It has also been the case that as the total number of reaction wells on a given card has increased, while the card size has remained constant, the wells have necessarily been formed increasingly close together. With the sample wells crowding each other on the card, it has become more likely that the sample contained in one well can travel to the next well, to contaminate the second well. The threat of increased contamination comes into play especially as card well capacity increases above 30 wells.

The current Vitek® 2 disposable product family uses a sample test card containing 64 individual sample wells into which chemicals can be dispensed for the identification and susceptibility testing of microorganisms in the diagnosis of infectious disease. Each of fill channels of the 64 well test card descend to and enter sample wells at an angle, which results in the natural flow of the sample fluid down through the fill channels by gravity, and resistance to small pieces of undissolved material flowing back up into the fluid circuitry. The fluid flow paths thoroughly dispersed over card, including both front and rear surfaces, also result in a longer total linear travel of the flowing fluid than conventional cards. The increased well-to-well distance leads to a reduction in the possibility of inter-well contamination. The average well-to-well distance of fluid flow channels on the 64 well card is to approximately 35 mm, significantly more than the 12 mm or so on many older card designs. The 64 well test card is further described, for example, in U.S. Pat. Nos. 5,609,828; 5,746,980; 5,869,005; 5,932,177; 5,951,952; and USD 414,272, the contents of which are incorporated herein by reference herein.

However, as previously discussed, the incubation carousel employed in the Vitek® 2 and Vitek® compact instruments rotates the test cards through a 360° rotation from a normal "upright" card position, through an "inverted" or "upside-down" card position and then back again to an "upright" position. This rotation of the card can lead to leaking of the sample well contents into the fill channels of prior art cards like the 64 well card where the fill channels descend to and enter sample wells at an angle. In the case of the 64 well card, the potential for well-to-well contamination is still mitigated by the large distance between wells. However, this requirement for longer distances between the wells limits the total number of wells that can fit on a test card of standard size.

In the case of identification, the use of 64 reactions wells tends to be sufficient. However, employing only 64 wells in determining antibiotic susceptibility is limiting. Increasing the number of wells in the card would allow improved performance by using more wells for a single antibiotic test as well as increase the number of antibiotics that could be evaluated in a single card. Accordingly, there is a need to increase the total well capacity in a standard test card while maintaining the reduction in the possibility of inter-well contamination. The novel test cards disclosed herein satisfy this goal without requiring significant changes to instruments designed to read each well during incubation.

SUMMARY OF THE INVENTION

We disclose herein design concepts for novel sample test cards that provide an increase in the total number of sample wells contained within a test card of standard dimensions. These design concepts are capable of delaying and/or preventing chemicals from migrating from one well to another during card filling and incubation.

In one possible design, a sample test card is provided comprising: (a) a card body defining a first surface and a second surface opposite the first surface, a fluid intake port and a plurality of sample wells disposed between the first and second surfaces, the first and second surfaces sealed with a sealant tape covering the plurality of sample wells; (b) a fluid channel network disposed in both the first surface and the second surface and connecting the fluid intake port to the sample wells, the fluid channel network comprising at least one distribution channels, a plurality of fill channels operatively connected to the at least one distribution channel, a plurality of through-channels operatively connected to one or more of the fill channels and a plurality of horizontally orientated fill ports operatively connecting the fill channels to the sample wells; and (c) wherein the test card comprises from about 80 to about 140 total sample wells. In other embodiments, a sample test card in accordance with this design concept may comprise 80, 88, 96, 104, 108, 112, 120, 126, 135 or 140 individual sample wells.

In another embodiment, the preset invention is directed to an improved sample test card being from about 90 to about 95 mm in width, from about 55 to about 60 mm in height and from about 4 to about 5 mm thick, having a substantially flat card body with a first surface and a second surface opposite to said first surface, an intake port formed in said card body, a plurality of sample wells formed in said card body, and a first fluid flow distribution channel, operatively connected to said intake port and traversing a portion of the first surface to distribute a fluid sample from said intake port to a first group of said sample wells and a second fluid flow distribution channel, operatively connected to said intake port traversing said second opposite surface to distribute a fluid sample from said intake port to a second group of said wells, said first and second fluid flow distribution channels thereby supplying fluid samples to said first and second groups of sample wells, wherein the improvement comprises said test card having from about 80 to about 140 total sample wells. In other embodiments, a sample test card in accordance with this design concept may comprise 80, 88, 96, 104, 108, 112, 120, 126, 135 or 140 individual sample wells.

In another possible design, a sample test card is provided comprising: (a) a card body defining a first surface and a second surface opposite the first surface, a fluid intake port and a plurality of sample wells disposed between the first and second surfaces, the first and second surfaces sealed with a sealant tape covering the plurality of sample wells; and (b) a fluid channel network connecting the fluid intake port to the sample wells, the fluid channel network comprising a first distribution channel disposed on the first surface, the first distribution channel comprising a fluid flow path from the fluid intake port to a plurality of second distribution channels or diffusion channels, wherein the second distribution channel or diffusion channels further comprise a plurality of diffusion barriers or "islands" operable to interrupt fluid flow between opposing sample wells, and wherein the second distribution channels or diffusion channels are operatively connected to the sample wells by a plurality of fill channels. In some embodiments, the test cards of this design concept may comprise from 80 to 140 individual sample wells, or from about 96 to about 126 individual sample wells, each of which receives a test sample, for example a biological sample extracted from blood, other fluids, tissue or other material of a patient, for spectroscopic or other automated analysis. In other embodiments, the sample test card in accordance with this design concept may comprise 80, 88, 96, 104, 108, 112, 120, 126, 135 or 140 individual sample wells.

BRIEF DESCRIPTION OF THE FIGURES

The various inventive aspects will become more apparent upon reading the following detailed description of the various embodiments along with the appended drawings, in which.

DETAILED DESCRIPTION OF THE INVENTION

Figure 1:
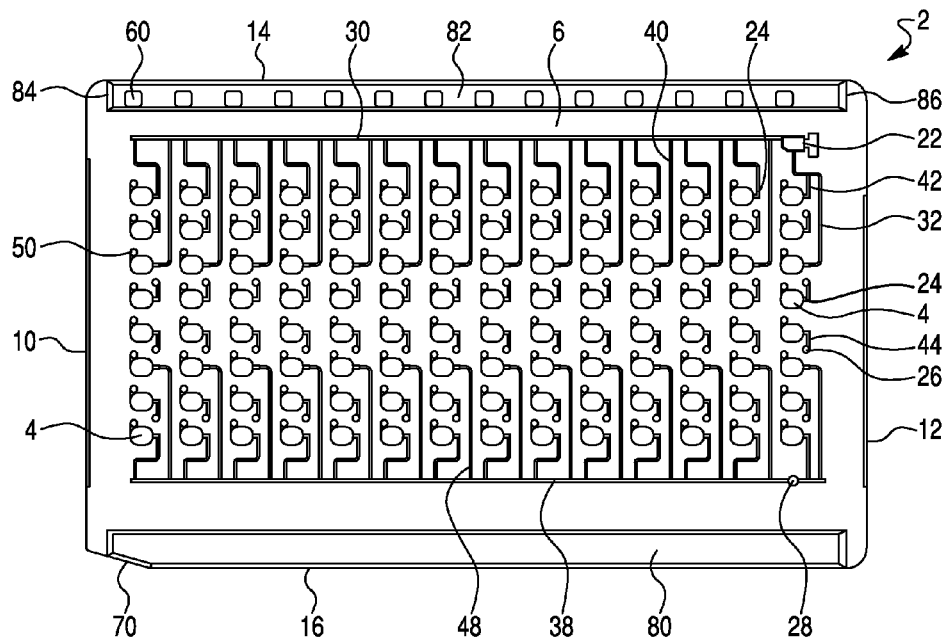
FIG. 1—is a front view of the front surface of a sample test card, in accordance with one design concept of the present invention. As shown, the sample test card comprises 112 sample wells, an intake reservoir, a plurality of distribution channels and a plurality of well ports.
Figure 2:
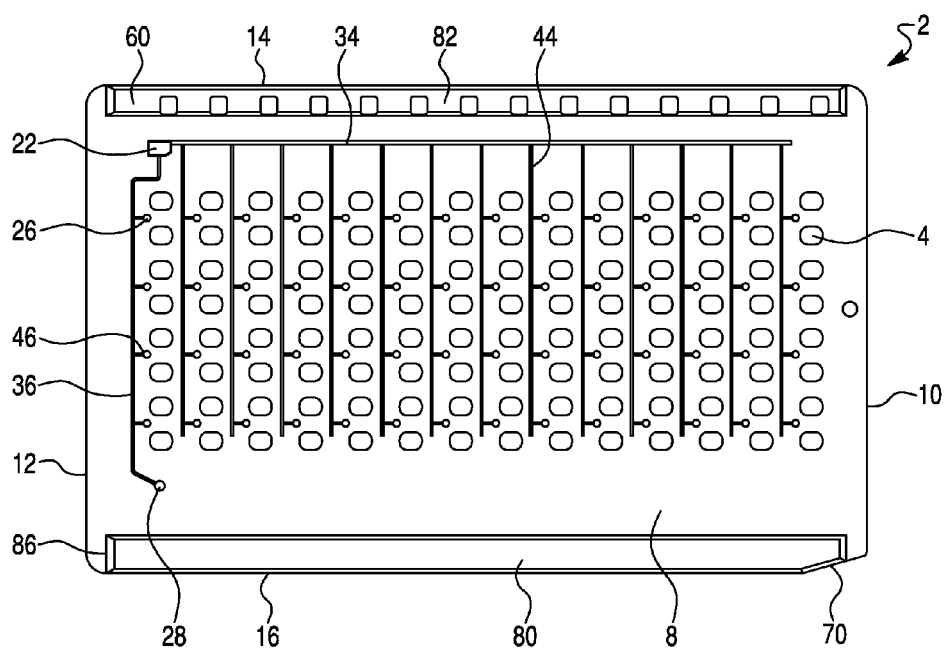
FIG. 2—is a front view of the rear surface of the sample test card shown in FIG. 1.
Figure 3:
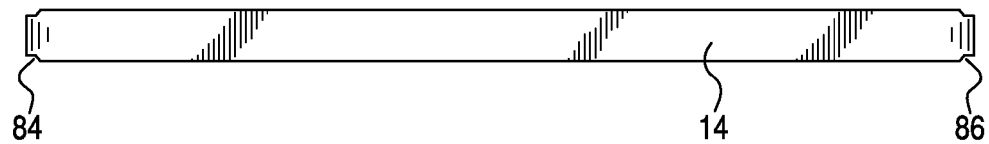
FIG. 3—is a top view showing the top edge of the sample test card of FIG. 1.
Figure 4:
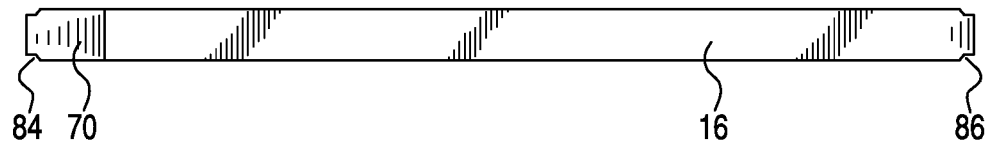
FIG. 4—is a bottom view showing the bottom edge of the sample test card of FIG. 1.
Figure 5:
FIG. 5—is a side view showing the first or leading side edge of the sample test card of FIG. 1.
Figure 6:
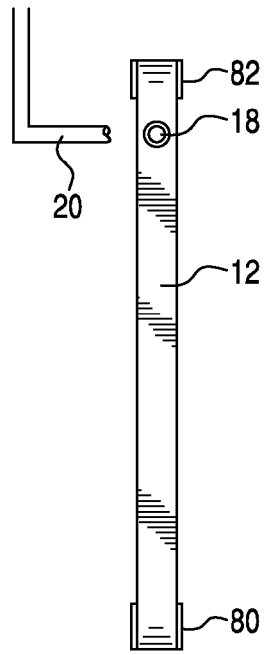
FIG. 6—is a side view showing the second or trailing side edge and intake port of the sample test card of FIG. 1.

The improved sample test cards of the present invention have a generally rectangular shape and are in standard dimensions of from about 90 to about 95 mm in width, from about 55 to about 60 mm in height and from about 4 to about 5 mm in thickness. In one embodiment, the sample test cards of the present invention are about 90 mm wide, about 56 mm high and about 4 mm thick. The test cards of this invention may comprise from 80 to 140 individual sample wells, or from about 96 to about 126 individual sample wells, each of which receives a test sample, for example a biological sample extracted from blood, other fluids, tissue or other material of a patient, for spectroscopic or other automated analysis. In other embodiments, the sample test cards may comprise 80, 88, 96, 104, 108, 112, 120, 126, 135 or 140 individual sample wells. The sample wells are typically arranged in a series of horizontal rows and vertical columns and may comprise from about 8 to about 10 rows of from about 10 to about 16 columns of wells. The biological sample may be a direct sample from the patient, or be a patient sample which is extracted, diluted, suspended, or otherwise treated, in solution or otherwise. Furthermore, in accordance with the present invention, the sample test card comprises a fluid channel network or a plurality of fluid flow channels (e.g., distribution channels and fill channels) for transport of a fluid test sample from an intake port to each of the individual sample wells. The distribution channels and fill channels (e.g., as schematically illustrated in FIGS. 1-2), may be preferably formed in full-radius style, that is, as a semicircular conduit, rather than a squared-off channel as in some older designs. The full-radius feature has been found by the inventors to reduce friction and fluid turbulence, further enhancing the performance of test card 2. The sample test cards are generally used in a landscape orientation.

The test cards may be made of polystyrene, PET, or any other suitable plastic or other material. The test cards may be tempered during manufacture with a softening material, so that crystalline rigidity, and resultant tendency to crack or chip, is reduced. Test cards for instance may be manufactured out of a blend of polystyrene, approximately 90% or more, along with an additive of butyl rubber to render the card slightly more flexible and resistant to damage. In some embodiments, the test cards may also be doped with coloring agents, for instance titanium oxide to produce a white color, when desired.

The test cards of the invention may be of use in identifying and/or enumerating any number of microorganisms, such as bacterial and/or other biological agents. Many bacteria lend themselves to automated spectroscopic, fluorescent and similar analysis after incubation, as is known in the art. The transmission and absorption of light is affected by the turbidity, density and colormetric properties of the sample. Fluorescent reactions may be performed as well, independently or along with spectroscopic or other measurements. If fluorescent data are gathered, use of a coloring agent in test cards may be preferred, since an opaque card reduces or eliminates the scattering of fluorescent emissions throughout the card, as can occur with a translucent material. Other types of detection and analysis can be done on the test cards, including testing of susceptibility of microorganisms to antibiotics of different types, and at different concentrations, so that the test cards are general-purpose instrument.

One design concept of the invention is illustrated in FIGS. 1-6. This design provides an improved sample test card 2, having a generally rectangular shape and in standard dimensions. The test card 2 further comprises a plurality of sample wells 4 and has a first or front surface 6 and a second or rear surface 8, opposite said front surface 6, a first or leading side edge 10, a second or trailing side edge 12, a top edge 14, and a bottom edge 16. The illustrated test card 2 of this embodiment contains a total of 112 individual sample wells 4, which extend completely through the test card from the front surface 6 to the rear surface 8, and each of which are capable of receiving a test sample for analysis, as previously described. As shown in FIGS. 1-2, the sample wells can be arranged in 8 rows of 14 columns of wells, thereby providing a total of 112 individual sample wells. However, as would be readily apparent to one of skill in the art, other well arrangements are possible.

To receive sample fluid, the test card 2 includes a sample intake plenum or port 18 (see FIG. 6), typically located on a perimeter edge (e.g., the second or trailing edge 16) in an upper right corner of the test card 2. The sample wells 4 of test card 2 contain dry biological reagents which are previously put in place in the sample wells 4, by evaporative, freeze-drying or other means. Each well 4 can hold a deposit of a different reagent that can be used for identifying different biological agents and/or for determining the antimicrobial susceptibility of different biological agents, as desired. The injected patient sample dissolve or re-suspend the dry biological reagents in each well 4 for analysis.

As is well known in the art, intake port 18 receives a fluid injection tip and related assembly (schematically illustrated as 20), through which the sample fluid or other solution which arrives to dissolve the biological reagents in each well 4 is injected, under a vacuum pulled on test card 2 (typically 0.7-0.9 PSIA), then released to atmospheric pressure. Injection port 18 includes a small intake reservoir 22 formed as a roughly rectangular hole through the test card 2, which receives incoming fluid, and acts as a fluid buffer. When the sample is injected into the card, a short segment of the sample tip can be pinched off or heat-sealed and left in place in intake port 18, acting as a sealing plug. After the test fluid (patient sample or other solution) enters the intake port 18 the fluid flows through a fluid flow path comprising a series of fluid flow channels (e.g., distribution channels and fill channels) for transport of a fluid test sample from the intake port 18 to each of the individual sample wells 4, as described in more detail herein.

It has been unexpectedly discovered that by employing the use of horizontally orientated well fill ports the average fluid flow path distance between wells can be reduced, thereby allowing for an increased well capacity, while maintaining strict inter-well contamination standards. Furthermore, it has also been discovered that by reducing the well sizes by approximately a third enough surface area is recovered to allow for an increased well capacity in a test card having standard dimensions.

As shown in the illustrated design concept (see FIGS. 1-2), the test card employs a fluid flow path comprising a plurality of distribution channels, fill channels, through-channels and well fill ports, which connects to, and fill, each of the individual sample wells with a test sample. Also, as shown, each of the well fill port connects to and enters the individual sample well in a generally horizontal or width-wise manner. Applicants have found that the use a horizontally orientated well fill port reduces the possibility of well leakage during rotation of the card in the carousel incubator of the Vitek® 2 or Vitek® compact instruments. Furthermore, in one design possibility, the well fill ports may have a width of about 0.5 to about 0.6 mm and a depth of about 0.5 to about 0.6 mm (i.e., a cross section of from about 0.25 to about 0.36 mm$^2$) In contrast, as disclosed elsewhere herein, the fill channels may have a width of about 0.2 to about 0.4 mm and a depth of about 0.3 to about 0.5 mm (i.e., a cross section of about 0.06 to 0.2 mm$^2$) While not wishing to be bound by theory, it is believed that this reduction in cross section from the well fill ports to the fill channels may act to further slow the migration of any fluid or chemicals that may have leak out of the individual sample wells and into the well fill ports.

As mentioned hereinabove, previous card designs employed the use of relatively long fluid flow paths between wells to increase the well-to-well distance between individual sample wells. The fluid flow paths thoroughly dispersed over the card, including both front and rear surfaces, resulted in an average well-to-well distance of approximately 35 mm. By contrast, in this design concept, the average flow channel distance between wells is less than 30 mm, or less than 25 mm. In another embodiment, the average well-to-well distance between individual sample wells 4 is from about 20 to about 25 mm. Again, Applicants have found that by employing the use of horizontally orientated well fill ports the average fluid flow path distance between wells can be reduced, thereby allowing for an increased well capacity, while maintaining strict inter-well contamination standards.

Accordingly, the combination of reduced well sizes, horizontally orientated well fill channels and shorter average well-to-well fluid flow path, has allowed for an increased well capacity within a test card having standard dimensions. The contamination rate is also reduced by the fact that the volume of the channels along the fluid circuit varies slightly along the overall circuit traveled by a given sample. That is, the through-channels, the main distribution channels and other segments of the paths have cross-sectional areas which, although all relatively fine, may differ slightly. The change in volume over the path tends to retard the progression of contamination, as do dog-legged or kinked sections of connecting conduits. The test cards of this design concept may comprise from 80 to 140 individual sample wells, or from about 96 to about 126 individual sample wells. In one embodiment, the sample test cards may comprise 80, 88, 96, 104, 108, 112, 120, 126, 135 or 140 sample wells.

Referring now to FIGS. 1-6, the illustrated test card 2 of this design concept will be described in further detail. As the test fluid (i.e., patient sample or other solution) enters intake port 18 it collects in intake reservoir 22 and travels along a first distribution channel 30 that leads away from the intake reservoir 22. First distribution channel 30 comprises a relatively long channel, which extends in a substantially horizontal or widthwise manner across the front surface 6 of the test card 2 and parallel to the top edge 14 of the card. In one embodiment the first distribution channel 30 may comprises a fluid flow channel having a width of about 0.5 mm and a depth of about 0.5 mm (i.e., a cross section of approximately 0.25 mm$^2$).

First distribution channel 30 is tapped at intervals along its length by a series or plurality of first fill channels 40, which generally descend from first distribution channel 30 toward the sample wells 4 in each of the fourteen illustrated columns. As shown in FIG. 1, first fill channels 40 are relatively short channels (which may be kinked) that extend down from first distribution channel 30 into respective well ports 24, which function to connect, and thereby fill the individual sample wells 4 located in the first and third rows (down from the top edge 14) of test card 2. In one embodiment, first fill channels 40 may comprise a fluid flow channel having a width of about 0.2 to about 0.4 mm and a depth of about 0.3 to about 0.5 mm (i.e., a cross section of about 0.06 to 0.2 mm$^2$) In another embodiment, the first fill channels 40 have a width of about 0.3 mm and a depth of about 0.4 mm (i.e., a cross section of about 0.12 mm$^2$).

Accordingly, the illustrated test card 2 (see FIGS. 1-2) therefore includes two rows (the first and third rows down from the top edge of the card) by thirteen columns of sample wells built up by connecting channels through the first distribution channel 30 and series of first fill channels 40. This provides a set of twenty-six (26) total sample wells that are filled via the first distribution channel 30.

Like the first distribution channel 30, the second distribution channel 32 is located on the front surface 6 of the test card 2 leading from the intake reservoir 22. The second distribution channel 32 descend vertically down (and which may be kinked, as shown) from the intake reservoir 22. The second distribution channel 32 leads to a second fill channel 42 and/or well ports 24, thereby connecting, and filling additional sample wells 4.

As shown the illustrated test card 2 includes two rows (again, first and third rows down from the top edge 14 of the card) by a single, or fourteenth column, of sample wells built up by connecting the second distribution channel 32 and/or second fill channel 42. Thus, two (2) sample wells that are filled via the second distribution channel 32.

In addition to the introduction of fluid through the path of first distribution channel 30 and first fill channels 40, fluid also travels to wells below the first and third row of wells through other fluid flow channels. More specifically, intake reservoir 22 also connects to a third distribution channel 34 formed on the opposite or rear surface 8 of the test card 2, which also leads away from the intake reservoir 22. The third distribution channel 34 extends substantially along the width of test card 2, generally parallel to the top edge 14 of the test card 2. In one embodiment, the third distribution channel 34 may comprise a fluid flow channels having a width of about 0.5 mm and a depth of about 0.5 mm (i.e., a cross section of approximately 0.25 mm$^2$).

Like the first distribution channel 30, the third distribution channel 34 is tapped above the fourteen illustrated columns of sample wells 4 by a series of third fill channels 44, each of which leads to series of through-channels 26. The through-channels 26 are small apertures, approximately 1 mm in diameter, formed cleanly through the body of test card 2, forming conduits or vias from one surface of the card to the other. The through-channels 26 are connected to additional well fill channels 44 on the front surface 6 of the card forming a short link to the respective well ports 24 and samples wells 4. Accordingly, the third fill channels 44 deliver the fluid to the sample wells from the opposite or rear side 8 of the test card 2, creating a different fluid flow circuit which extends from intake reservoir 22. That is, this path involves the third distribution channel 34 and third fill channels 44 on the rear surface of the card, through the body of the card by way of through-channels 26, then out to connecting short fill channels 44 and well ports 24 which deliver the sample to the well 4. In one embodiment, third fill channels 44 may comprise a fluid flow channel having a width of about 0.2 to about 0.4 mm and a depth of about 0.3 to about 0.5 mm (i.e., a cross section of about 0.06 to 0.2 mm$^2$) In another embodiment, the third fill channels 44 have a width of about 0.3 mm and a depth of about 0.4 mm (i.e., a cross section of about 0.12 mm$^2$).

In the illustrated test card of FIGS. 1-2, the third distribution channel 34 leads to thirteen third fill channels 44, each of which leads to four through-channels 26 and subsequently to four individual sample wells 4. Accordingly, the illustrated test card 2 therefore includes four rows (the second, fourth, fifth and seventh rows down from the top edge of the card) by thirteen columns of sample wells built up by connecting channels through the third distribution channel 34 and series of third fill channels 44. This provides a set of 52 total sample wells that are filled via the third distribution channel. Likewise, in the illustrated test card (see FIGS. 1-2) each of the thirteen third fill channels 44 leads to four through-channels 26, giving a total of 52 fill-channels 44.

A fourth distribution channel 36 also leads away from the intake reservoir 22 on the rear surface 8 of the test card 2. The fourth distribution channel 36 descends substantially vertically along the rear surface 8 of the card 2 parallel to the first 10 and second 12 side edges of the card 2. Like the other distribution channels described above, in one embodiment, the fourth distribution channel 36 may comprise a fluid flow channels having a width of about 0.5 mm and a depth of about 0.5 mm (i.e., a cross section of approximately 0.25 mm$^2$).

The fourth distribution channel 36 first leads to a series or plurality of fourth fill channels 46, which comprise short channels located on the rear surface 8 of the test card 2, each of which leads to a through-channel 26 forming a conduit or via from one surface of the card to the other, and which are subsequently connected to additional short fill channels 46 on the front surface 6 of the card 2. The fill channels 46 on the front surface 6 of the card 2 form a short link to the respective well ports 24 and samples wells 4. Like the third fill channels 44, the fourth fill channels 46 deliver the fluid to the sample wells 4 from the opposite or rear side 8 of the test card 2, creating a different fluid flow circuit, which extends from intake reservoir 22.

As shown the illustrated test card 2, the fourth distribution channel 36 leads to four through-channels 26 each of which subsequently lead to an individual sample well 4 in second, forth, fifth and seventh rows (i.e., the second, fourth, fifth and sixth rows down from the top edge of the card) of the fourteenth column on the front surface 6 of the test card 2. Accordingly, four (4) sample wells that are filled via the fourth distribution channel 36 and associated through-channels 26.

The fourth distribution channel 36 also leads to a distribution through-channel 28 located in the bottom corner of the test card 2, and which leads through the card to a fifth distribution channel 38 located in the front surface 6 of the test card 2. More specifically, the fourth distribution channel 36 is in fluid connection with intake reservoir 22, but traces a generally vertical path downward from the reservoir to a distribution through-channel 28, located at a lower right section of the test card 2. Fluid flows down through the fourth distribution channel 36, into the distribution through-channel 28, through the card from the rear surface 8 to the front surface 6, and then into the fifth distribution channel 38. The fifth distribution channel 38, located on the front surface 6 of test card 2, extends along the lower base of the card 2 in a generally horizontal or widthwise manner parallel to the bottom edge 16 of the card. In one embodiment, the fifth distribution channel 38 may comprise a fluid flow channels having a width of about 0.5 mm and a depth of about 0.5 mm (i.e., a cross section of approximately 0.25 mm$^2$).

Rising up from the fifth distribution channel 38 are a series or plurality of fifth fill channels 48, which generally resemble the first fill channels 40 but which extend upward from fifth distribution channel 38, rather than downward. However, fifth fill channels 48 perform the same basic function, delivering the fluid to a series of well ports 24 and subsequently to individual sample wells 4.

The illustrated test card 2 (see FIGS. 1-2) therefore includes two rows (the sixth and eighth rows down from the top edge of the card) by thirteen columns of sample wells built up by connecting channels through the fourth 36 and fifth 38 distribution channel and series of fifth fill channels 48. This provides a set of twenty-six (26) total sample wells that are filled via the first distribution channel 30.

Accordingly, as mentioned elsewhere herein, the illustrated test card 2 of FIGS. 1-6, therefore includes eight rows by fourteen columns of sample wells (i.e., 112 total individual sample wells) built up by a plurality of distribution channels, fill channels and through-channels distributed over the front 6 and rear 8 surfaces of the test card 2.

Also, as shown in FIGS. 1-2, each of the individual sample wells 4 includes an associated bubble trap 50, connected to sample well 4 at an upper corner of the well, and located at a height slightly above the well 4 on the front card surface 6. As known in the art, each bubble trap 50 is connected to its respective well 4 by a short trap connecting conduit 52, formed as a hollow passage part-way into the card surface and forming a short conducting path for trapped gaseous bubbles which have been formed in, or communicated to, the well 4 during the injection operation, by bacterial or other biological reaction, or otherwise. Bubble trap 50 does not cut through the card completely, instead consisting of a depression or well of roughly oval shape, optionally with a rounded bottom contour, and a volume of from about 2 to about 4 cubic mm in the illustrated embodiment. Because the bubble trap 50 is located at an elevated position above each respective well 4, any gaseous bubbles will tend to rise and be trapped in the depression of trap 50. With gaseous remnants led off to the bubble trap 50, analytical readings on the biological sample can be made more reliably, since scattering and other corruption of the microbial radiation reading by gas is reduced or eliminated.

The sample wells 4 which receive the fluid from the second distribution through-channel circuit, like the sample wells which receive the fluid through the (front-planar) first distribution channel, also have bubble traps 50 associated with them, in the same general above-well configuration.

For mechanical interaction with the automated reading machine, test card 2 may also be provided with a series of sensor stop holes 60, located along the uppermost edge of the card. Sensor stop holes 60, illustrated as regularly spaced, rectangular through-holes, permit associated photo-detectors to detect when a test card 2 mounted in a reading machine has come into proper alignment for optical reading. In prior art cards, the sensor stop holes were arranged in vertical register with the vertical columns of wells, so that the optical detection of the stop hole corresponds exactly to positioning of the sample wells before optical reading devices. However, it has now been discovered that this precise alignment of the sensor stop holes with the leading edge of the sample wells can lead to the front edge of the well not being read as a result of a slight delay in the stopping of the card once the sensor stop holes are detected, and thus, a slight misalignment for optical reading. Accordingly, in the present embodiment, the sensor stop holes 60 are arranged in a vertical alignment slightly ahead of the vertical column of wells 4, so that one optical detection of the stop holes 60 occurs and optical reading of the test card 2 initiated, the reading will start at the front edge of the sample well 3. In accordance with this embodiment, the sensor stop holes 60 may be aligned from about 0.25 to about 2 mm ahead (i.e., closer to the first or leading edge of the test card 2) of the vertical wells 4. Moreover, aligning the sensor stop holes slightly ahead of the leading edge of the sample well enables the use of smaller sample wells since the full width of the well can be read by the optical reading machine.

Another advantage of test card 2 of the illustrated design is that patient sample and other markings are not introduced directly on the card itself, in pre-formed segments, as for example shown for example in U.S. Pat. No. 4,116,775 and others. Those on-card striplings and markings can contribute to debris, mishandling and other problems. In the invention, instead, the card 2 may be provided with bar-coding or other data markings (not shown) by adhesive media, but markings or pre-formed information segments are not necessary (though some could be imprinted if desired) and debris, mishandling, loss of surface area and other problems can be avoided.

Test card 2 furthermore includes, at the lower left corner of the card as illustrated in FIG. 1, a tapered bezel edge 70. Tapered bezel edge 70 provides an inclined surface for easier insertion of test card 2 into, carrousels or cassettes, into slots or bins for card reading, and other loading points in the processing of the card. Tapered bezel edge 70 provides a gently inclined surface, which relieves the need for tight tolerances during loading operations.

Test card 2 also includes a lower rail 80 and an upper rail 82, which are slight structural "bulges" at along the top and bottom areas of the card to reinforce the strength and enhance handling and loading of the test card 2. The extra width of lower and upper rails 80 and 82 also exceeds the thickness of sealing material, such as adhesive tape, that is affixed to the front 6 and rear 8 surfaces of test card 2 for sealing during manufacture and impregnation with reagents. The raised rails therefore protect that tape, especially edges from peeling, during the making of the test card 2, as well as during handling of the card, including during reading operations.

As is well known in the art, upper rail 82 may have serrations (not shown) formed along its top edge, to provide greater friction when test card 2 is transported in card reading machines or otherwise using belt drive mechanisms. Also, as well known in the art, lower card rail 80 may also have formed in it reduction cavities (not shown), which are small elongated depressions which reduce the material, weight and expense of the card by carving out space where extra material is not necessary in the reinforcing rail 80.

In terms of sealing of test card 2 to contain reagents and other material, it has been noted that sealing tapes are typically used to seal flush against test card 2 from either side, with rail protection. Test card 2 may also includes a leading lip 84 on lower card rail 80, and on upper card rail 82. Conversely, at the opposite end of the test card 2 there may also be a trailing truncation 86 in both rails. This structure permits sealing tape to be applied in the card preparation process in a continuous manner, with card after card having tape applied, then the tape cut between successive cards without the tape from successive cards getting stuck together. The leading lip 84 and trailing truncation 86 provides a clearance to separate cards and their applied tape, which may be cut at the trailing truncation 86 and wrapped back around the card edge, for increased security against interference between abutting cards. Thus, the trailing truncation or slanted ramp feature 86 ends slightly inward from the extreme edge of the ends of the card, as shown in FIGS. 1 and 2 to define a portion of the card surface or "shelf portion" between the ends of the ramps 86 and the second or trailing edge 12 of the test card 2, extending across the width of the test card 2. This shelf portion provides a cutting surface for a blade cutting the tape applied to the card. Further, the ramp 86 facilitates the stacking of multiple test sample cards without scuffing of the sealant tape applied to said cards, by allowing the ramps to slide over each other during a stacking motion with the raised rails preventing scuffing of the tape.

Figure 7:
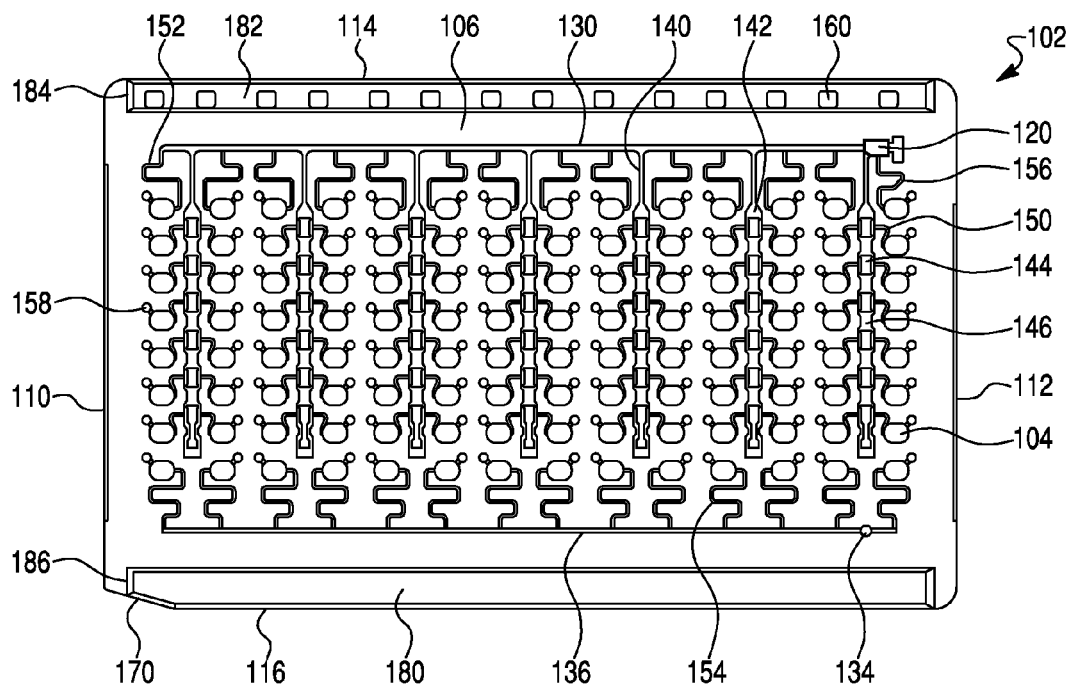
FIG. 7—is a front view of the front surface of a sample test card, in accordance with another design concept of the present invention. As shown, the sample test card comprises 112 sample wells, an intake reservoir, a plurality of distribution channels and a plurality of well ports.
Figure 8:
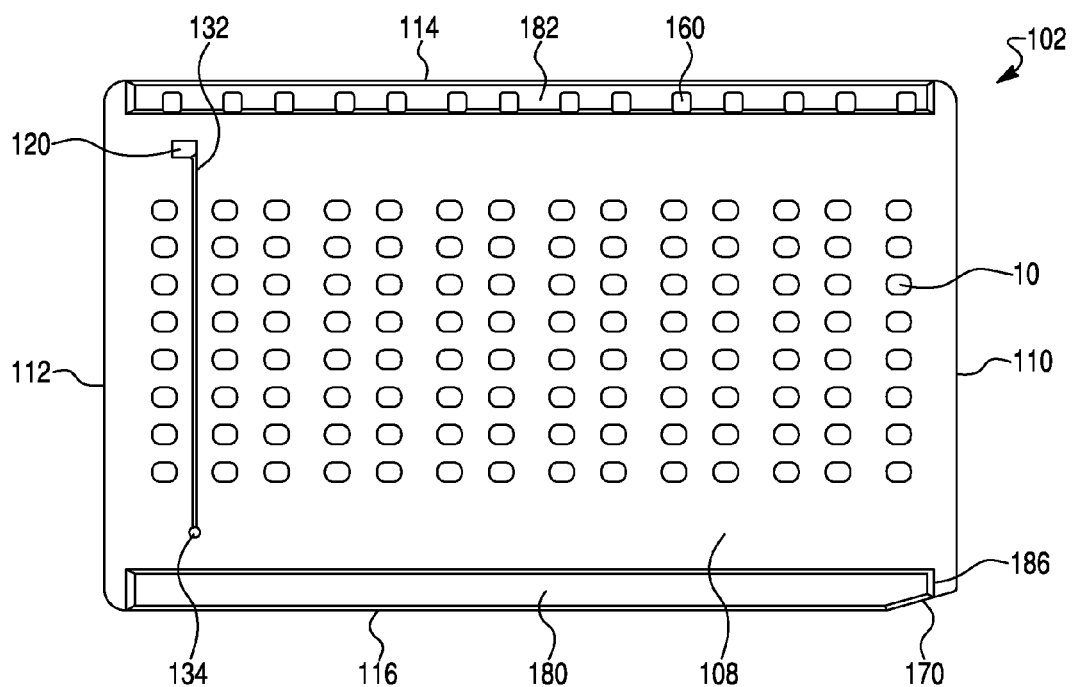
FIG. 8—is a front view of the rear surface of a sample test card, in accordance with the design concept of FIG. 7. As shown, the sample test card comprises 112 sample wells and an intake reservoir.

In another design concept of the invention is illustrated in FIGS. 7-8. Like the test card shown in FIGS. 1-6, the design concept illustrated in FIGS. 7-8 provides an improved sample test card 102, having a generally rectangular shape and in standard dimensions. The test card 102 further comprises a plurality of sample wells 104 and has a first or front surface 106 and a second or rear surface 108, opposite said front surface 106, a first or leading side edge 110, a second or trailing side edge 112, a top edge 114, and a bottom edge 116. The illustrated test card 102 of this embodiment contains a total of 112 individual sample wells 104, which extend completely through the test card from the front surface 106 to the rear surface 108, and each of which are capable of receiving a test sample for analysis, as previously described. However, test cards of this design may comprise from 80 to 128 individual sample wells, or from about 96 to about 140 individual sample wells. In one embodiment, the sample test cards may comprise 80, 88, 96, 104, 108, 112, 120, 126, 135 or 140 sample wells. The sample wells are typically arranged in a series of horizontal rows and vertical columns and may comprise from about 8 to about 10 rows of from about 10 to about 16 columns of wells. As shown in FIGS. 7-8, the sample wells 104 can be arranged as fourteen columns of eight wells 104 (i.e., 112 total sample wells).

As with the illustrated test card design shown in FIGS. 1-6, this design concept will also receive a sample fluid through an intake plenum or port (not shown), typically located on a perimeter edge. As is well known in the art, intake port receives a fluid injection tip and related assembly (not shown), through which the sample fluid or other solution which arrives to dissolve the biological reagents in each well 104 is injected, under a vacuum pulled on test card 102 (typically 0.7-0.9 PSIA), then released to atmospheric pressure. Also like the first design concept (see FIGS. 1-6), the injection port of this design will include a small intake reservoir 120 formed as a roughly rectangular hole through the test card 102, which receives incoming fluid, and acts as a fluid buffer. When the sample is injected into the card, a short segment of the sample tip can be pinched off or heat-sealed and left in place in intake port, acting as a sealing plug. After the test fluid (patient sample or other solution) enters the intake port the fluid will flow through a fluid flow path comprising a series of fluid flow channels (e.g., distribution channels and fill channels) for transport of a fluid test sample from the intake port to each of the individual sample wells, as described in more detail hereinbelow.

As shown in FIGS. 7-8, the illustrated test card 102 employs a fluid flow path comprising a first distribution channel 130, a second distribution channel 132, a through-hole 134, a third distribution channel 136, a plurality of diffusion channels 142, and a plurality of fill channels 150, 152, 154 and 156, which connect to, and fill, each of the individual sample wells with a test sample. Also, as shown in FIG. 7, the plurality of diffusion channels 142 further comprises a series or plurality of diffusion barriers or "islands" 144, which are located within the diffusion channel between opposing fill channels 150 and operate to interrupt or impede fluid flow between opposing sample wells 104. Also, as shown in FIG. 7, the diffusion channels 144 further comprise diffusion zones 146, which comprise a large cross sectional area of the diffusion channel between the diffusion barriers or "islands" 144.

As previously described hereinabove, after a test card is filled with a test sample, the dense media contained in each of the wells may flow, or leak, out of the wells and into the fluid flow channels during incubation of the test card. Once in the fill channels any media that has leaked out may subsequently flow to adjacent sample wells, thereby contaminating those sample wells.

Applicants have discovered that by employing flow channels (i.e., diffusion channels 142) having a large cross sectional area and/or diffusion zones 146, which contain a large volume of the test sample, allows for any media that has leaked out of a sample well to be diluted, thereby reducing the potential for well-to-well contamination. Furthermore, Applicants have discovered that by including features, such as diffusion barriers or "islands" 144, in the flow channels (i.e., diffusion channel 142), which operate to disrupt or impede the flow path between wells, the potential effects of well-to-well contamination can be further mitigated because the diffusion barriers 144 act to re-route any media that may have leaked out of the sample wells to the diffusion zones 146. More specifically, the use of diffusion bathers 144 which disrupt of impede the fluid flow path between wells, forces any media that may have leaked out of the sample wells to travel through the diffusion zones 146, which are larger cross-section areas of the flow channels which contain a relatively larger amount of the test sample loaded into the test card, thereby allowing for dilution of any leaked media. By introducing features to dilute any media that has leaked out of a well, the long fluid flow paths between wells required in previous card designs can be decreased. The use of a shorter fluid flow path between wells allows for an increased well capacity within a test card, while maintaining strict inter-well contamination standards. Furthermore, by reducing the well sizes by approximately a third enough surface area is recovered to allow for an increased well capacity in a test card having standard dimensions.

Referring now to FIGS. 7-8, the illustrated test card 102 of this design concept will be described in further detail. As shown in FIGS. 7-8 the test card 102 may comprise 112 individual sample wells arranged in fourteen columns of eight sample wells 104. As the test fluid (i.e., patient sample or other solution) enters intake port it collects in intake reservoir 120 and travels along a first distribution channel 130 that leads away from the intake reservoir 122. First distribution channel 130 comprises a relatively long channel, which extends in a substantially horizontal or widthwise manner across the front surface 106 of the test card 102, and parallel to the top edge 114 of the card. In one embodiment the first distribution channel 130 may comprises a fluid flow channel having a width of about 0.5 mm and a depth of about 0.5 mm (i.e., a cross section of approximately 0.25 mm$^2$).

First distribution channel 130 is tapped at intervals along its length by a series or plurality of diffusion channels 142, which generally descend from the first distribution channel 130 between columns of sample wells 104. As shown, for example in FIG. 7, the diffusion channel 142 may comprise a narrow entrance channel 140 that directly taps the first distribution channel 130 and the main channel or diffusion channel body 142. Also, as shown, the test card 102 may comprise 14 columns of 8 sample wells (i.e., 112 total wells).

In the embodiment shown in the figures, test card 102 comprises a set of seven total diffusion channels 142, each connected to a plurality of sample well 104 via a plurality of first fill channels 150. Also as shown, each of the diffusion channels 142 further provides a diffusion barrier 144, which disrupts the flow and a diffusion zone 146, which operates to dilute any media that has leaked out of a sample well 104. In one embodiment, the diffusion channel 142 comprises a fluid flow channel having a width of about 2 mm, and a depth of about 0.6 mm. Furthermore, as discussed above, the diffusion channel 132 may comprise therein a plurality of diffusion barriers 144 which act to which operate to disrupt or impede the flow path between wells. In general, the diffusion barriers 144 are placed within the diffusion channel 142 between opposing sets of sample wells 104, and can be spaced apart by about 2 mm within the second distribution channel 132, thereby creating the diffusion zones 146. The diffusion barriers 144 themselves can be about 1.2 mm in width and about 2 mm in height. The diffusion zones 146 provides for a dilution reservoir within the diffusion channel 142 located between opposing sample wells 104. The diffusion zones 146 generally have a width of about 2 mm, a height of about 2 mm and depth of about 0.6 mm (i.e., a volume of about 2.4 mm$^3$).

As shown in FIGS. 7-8, the sample test card 102 further comprises a second distribution channel 132 located on the rear surface 108 of the test card 102. In the exemplified design of FIGS. 7-8, the second distribution channel 132 comprises a relatively long channel, which extends in a substantially vertical manner down the rear surface 108 of the test card 102, and parallel to the second or trailing side edge 112 of the card 102. The second distribution channel 132 leads to a through channel 134 located in the bottom corner of the test card 102, through the card, and subsequently to a third distribution channel 136 located on the front surface 106 of the card. Third distribution channel 136 comprises a relatively long channel, which extends in a substantially horizontal or widthwise manner across the front surface 106 of the test card 102, and parallel to the bottom edge 116 of the card. In one embodiment the second distribution channel 132 and third distribution channel 136 may comprises a fluid flow channel having a width of about 0.5 mm and a depth of about 0.5 mm (i.e., a cross section of approximately 0.25 mm$^2$).

As shown in FIGS. 7-8, the sample test card 102 comprises a plurality of fill channels 150, 152, 154 and 156, which are operably connected to, and fill individual sample wells 104. The fill channels 150, 152, 154 and 156 are relatively short channels (which may be kinked) that extend horizontally and/or vertically from the distribution channels 130 and/or diffusion channels 142, which function to connect, and thereby fill the individual sample wells 104 of test card 102. In general, providing kinked fill channels, which extend vertically and horizontally across the surface of the test card, allows for increased channel length, thereby reducing and/or eliminating the possibility of well-to-well contamination. In the exemplified embodiment of FIGS. 7-8, a plurality of first fill channels 150 connect the diffusion channels 146 with, and thereby fill, a set of first sample wells 104. A plurality of second fill channels 152 lead from, or tap, the first distribution channel 130, connecting the first distribution channel 130 with, and thereby filling, a second set of individual sample wells 104. Also as shown, a plurality of third fill channels 154 lead from, or tap, the third distribution channel 136, connecting the third distribution channel 136 with, and thereby filling, a third set of individual sample wells 104. Furthermore, as shown, a fourth fill channel 156 may be provided that connects the intake reservoir 120 with, and thereby fills, an individual sample well 104. In one embodiment, the plurality of fill channels 150, 152, 154 and 156 may comprise fluid flow channels having a width of about 0.2 to about 0.4 mm and a depth of about 0.3 to about 0.5 mm (i.e., a cross section of about 0.06 to 0.2 mm$^2$). In another embodiment, the fill channels 134 have a width of about 0.3 mm and a depth of about 0.4 mm (i.e., a cross section of about 0.12 mm$^2$).

Accordingly, the illustrated test card 102 (see FIGS. 7-8) includes fourteen columns each having eight sample wells, built up by connecting channels through a fluid flow path comprising the first, second and third distribution channels 130, 132 and 136, diffusion channels 142 and fill channels 150, 152, 154 and 156. This provides a set of one hundred and twelve (112) total sample wells that are filled by the fluid flow path of this design concept.

As described above in relation to the first design concept (see FIGS. 1-6), the design concept illustrated in FIGS. 7-8 may further comprise a plurality of bubble traps 158, associated with, or connected to, each of the individual sample wells 104. The test cards 102 of this design concept may also comprise a series of sensor stop holes 160, a barcode or other data marking (not shown), a tapered bezel edge 170, and/or lower and upper rails 180, 182, optionally with associated leading lip 184 or trailing truncation 186, as described in more detail hereinabove.

The foregoing description of the improved test cards of the invention is illustrative, and variations on certain aspects of the inventive system will occur to persons skilled in the art. The scope of the invention is accordingly intended to be limited only by the following claims.

That which is claimed is:
1. A sample test card, comprising:
(a) a card body defining:

a first surface and a second surface opposite said first surface, such that the first surface faces an opposite direction from the second surface,
a fluid intake port, and
a plurality of sample wells disposed between said first and second surfaces, said first and second surfaces sealed with a sealant tape covering said plurality of sample wells; and
(b) a fluid channel network disposed in both said first surface and said second surface and connecting said fluid intake port to said sample wells, said fluid channel network comprising:
at least one distribution channel,
a plurality of fill channels connected to said at least one distribution channel, said fill channels comprising a first fill channel disposed in said first surface and a second fill channel disposed in said second surface,
a plurality of through-channels connected to one or more of said second fill channels and forming a conduit to the first fill channel on the first surface, and
a plurality of horizontally oriented fill ports connecting said second fill channels to said sample wells, wherein each of the fill ports extends in a widthwise direction of the card body, wherein each of the fill ports extends perpendicular to a portion of the second fill channels, wherein said fill channels have a reduced cross-section compared to said fill ports.

2. The test card of claim 1, wherein said test card comprises 96 sample wells arranged as twelve columns of eight sample wells.

3. The test card of claim 1, wherein said test card comprises 112 sample wells arranged as fourteen columns of eight sample wells.

4. The test card of claim 1, wherein said horizontally orientated fill ports comprise a width of about 0.5 to about 0.6 mm and a depth of about 0.5 to about 0.6 mm.

5. The test card of claim 1, further comprising bubble traps in fluid communication with said sample wells, said traps being positioned at least partly above said wells.

6. The test card of claim 1, wherein the average fluid channel network distance between wells is from about 20 to about 25 mm.

7. The test card of claim 1, wherein the fluid channel network further comprises a second distribution channel disposed on said first surface of said test card and operatively connected to a second set of sample wells.

8. The test card of claim 7, wherein the fluid channel network further comprises a third distribution channel, a plurality of third fill channels and a plurality of through-channels disposed on said first and said second surface of said test card and operatively connected to a third set of sample wells.

9. The test card of claim 8, wherein the fluid channel network further comprises a fourth distribution channel, a plurality of fourth fill channels and a plurality of through-channels disposed on said first and said second surface of said test card and operatively connected to a fourth set of sample wells.

10. The test card of claim 9, wherein the fluid channel network comprises a fifth distribution channel and a plurality of fifth fill channels disposed on said first surface of said test card and operatively connected to a fifth set of sample wells.

11. The test card of claim 1, further comprising sensor stop holes for aligning the card for optical readings.

12. The test card of claim 11, wherein said sensor stop holes are aligned from about 0.25 mm to about 2 mm ahead of each of said columns of sample wells.

13. The test card of claim 1, wherein the average fluid channel network distance between wells is less than 30 mm.

14. The test card of claim 1, wherein the plurality of fill ports are perpendicular to the at least one distribution channel.

15. The test card of claim 1, wherein the first fill channels are perpendicular to the at least one distribution channel at a junction between the first fill channels and the at least one distribution channel.

16. The test card of claim 1, wherein the widthwise direction is defined parallel to a longest edge of the card body, and wherein each of the fill ports is oriented parallel to the longest edge of the card body.

17. The test card of claim 1, wherein the fill ports terminate at respective ones of the sample wells.

18. The test card of claim 1, wherein said test card comprises from about 80 to about 140 total sample wells.

* * * * *